United States Patent [19]

Pomidor et al.

[11] Patent Number: 4,663,466

[45] Date of Patent: May 5, 1987

[54] PROCESS FOR PREPARING SUBSTITUTED AMINO HERBICIDES

[75] Inventors: Patricia B. Pomidor, Fremont; Carl E. Ward, San Jose, both of Calif.

[73] Assignee: Chevron Research Company, San Francisco, Calif.

[21] Appl. No.: 801,273

[22] Filed: Nov. 25, 1985

Related U.S. Application Data

[63] Continuation-in-part of Ser. No. 666,078, Oct. 26, 1984, abandoned.

[51] Int. Cl.[4] .................. C07D 333/36; C07D 307/02; C07D 401/00; C07D 405/00

[52] U.S. Cl. ...................................... 549/68; 549/480; 546/283; 546/284; 548/517; 548/527

[58] Field of Search .................. 549/68, 480; 546/283, 546/284; 548/517, 527

[56] References Cited

PUBLICATIONS

Tetrahedron, vol. 24, p. 5655 (1968).

*Primary Examiner*—Alan Siegel
*Attorney, Agent, or Firm*—S. R. LaPaglia; T. G. DeJonghe; L. S. Squires

[57] ABSTRACT

Processes for alkylating certain 3-oxo-4-substituted phenyl-5-amino-2,3-dihydrofurans and 2,3-dihydrothiophenes. The process effects replacement of the 5-amino group with a new amino group having the desired substitution. The products are useful as herbicides.

33 Claims, No Drawings

PROCESS FOR PREPARING SUBSTITUTED AMINO HERBICIDES

CROSS-REFERENCE TO RELATED APPLICATIONS

This application is a continuation-in-part of commonly assigned application Ser. No. 666,078, filed Oct. 26, 1984, now abandoned.

BACKGROUND OF THE INVENTION

This invention relates to improved processes for preparing 5-substituted amino-3-oxo-4-(substituted phenyl)-2,3-dihydrofuran and 2,3-dihydrothiophenes. The products are especially useful as herbicides.

Commonly assigned U.S. application Ser. No. 607,610, filed May 9, 1984, Carl E. Ward, discloses herbicidal compounds having the generic formula:

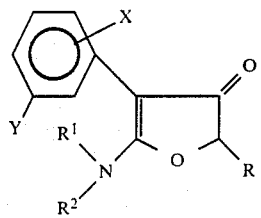

wherein R, $R^1$, $R^2$, X and Y can be certain substituents as will be subsequently defined.

Also in commonly-assigned U.S. application Ser. No. 623,805, filed June 22, 1984, C. E. Ward discloses compounds having the formula:

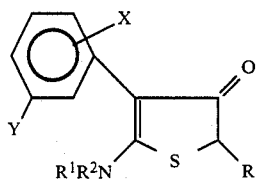

wherein R, $R^1$, $R^2$, X and Y can be certain substituents as will be subsequently defined.

The disclosures of said U.S. applications Ser. Nos. 607,610 and 623,805 are hereby incorporated by reference in their entirety.

In accordance with the teachings of theses applications, the compounds of Formulas I and II wherein one or both of $R^1$ and/or $R^2$ are other than hydrogen are prepared by a fairly complicated alkylation of the corresponding primary or secondary amine of Formulas I and II.

The Journal of Organic Chemistry, Vol. 49, p. 228 (1984) describes the preparation of 1-aryl-2-amino-5-oxocyclopent-1-ene via the reaction of ammonia or ammonium hydroxide with 1-aryl-2-chloro-5-oxocyclopent-1-ene. Synthesis p. 902 (1983) describes the amination of certain 1-hydroxy-2-acylethylene derivatives with quaternary acetate salts (e.g., $R^4NH_3OAc$) to yield the corresponding 1-($R^4$-amino)-2-acylethylene derivative. Other aminations are described in Chemiker-Zeitung Vol. 104, p, 302 (1980) and Tetrahedron, Vol. 24, p, 5655 (1968).

SUMMARY OF THE INVENTION

The present invention describes a relatively simple and convenient method for preparing the secondary and tertiary amines of Formulas I and II given hereinabove. In addition, the present process affords improved yields in many cases. The present process further typically provides a cleaner reaction with fewer side products. The present process is further more selective and can be readily used to prepare monosubstituted amino substitution whereas other processes, such as phase transfer amination reactions, generally produce substantial amounts of disubstituted amino products.

The present process can be effected by contacting the compounds of Formulas I and II with a primary or secondary amine having the desired substitution in a liquid alcohol under reactive conditions, preferably in the presence of an acid salt of a primary, secondary or tertiary amine. The process effects replacement of the entire 5-amino group from the starting material with the amine group used in the reaction. Where the primary amines of Formulas I and II are used as starting materials, the process is especially efficient.

The invention will be further described hereinbelow.

FURTHER DESCRIPTION OF THE INVENTION AND PREFERRED EMBODIMENTS

The present process can be schematically represented by the following overall reaction equation:

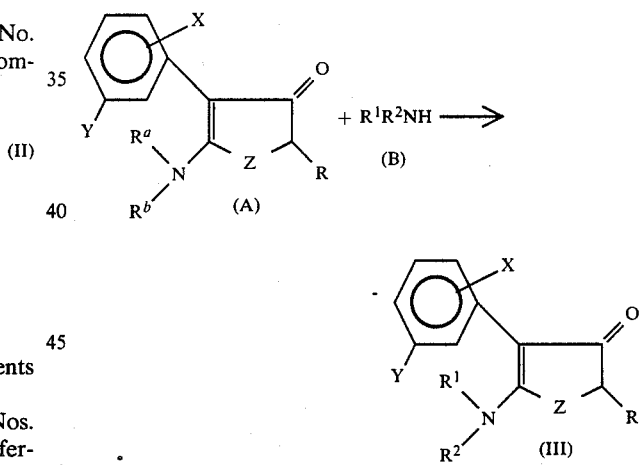

wherein R is lower alkyl having 1 through 4 carbon atoms, cycloalkyl having 3 through 7 carbon atoms, lower alkenyl having 2 through 6 carbon atoms; fluoroalkyl having 1 through 4 carbon atoms and 1 through 3 fluoro atoms; haloalkenyl having 2 through 4 carbon atoms and 1 through 3 halo atoms independently selected from the group of fluoro, chloro, bromo, or iodo and wherein the halo atom is on a double bond carbon atom; lower alkoxyalkyl wherein the alkoxy and alkyl moiety thereof independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein said aryl moiety is phenyl, naphth-1-yl or inden-1-yl; or substituted aryl or arylalkylene selected from the group having the formulas:

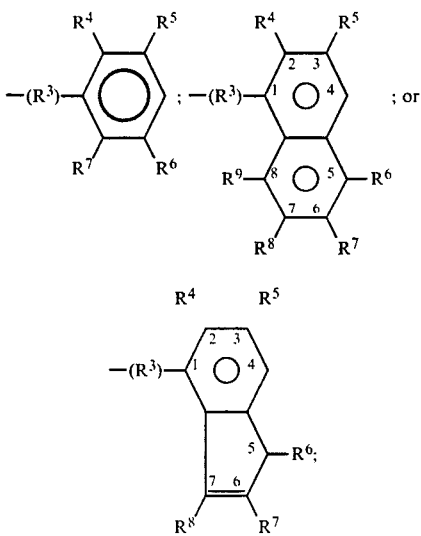

wherein
one, two or three of $R^4$, $R^5$, $R^6$, $R^7$, $R^8$, and $R^9$ are independently selected from the group of lower alkyl, lower alkoxy, halo, nitro, or fluoroalkyl having 1 through 3 carbon atoms and 1 through 3 fluoro atoms, and the remainder are hydrogen; and $R^3$ is a single bond or an alkylene having 1 through 3 carbon atoms;

$R^1$ is hydrogen or alkyl having 1 through 4 carbon atoms, $R^2$, $R^a$ and $R^b$ are independently hydrogen, alkyl having 1 through 4 carbon atoms, alkenylmethylene having 3 or 4 carbon atoms; alkoxycarbonylalkyl having from 1 through 4 carbon atoms in the alkoxy moiety, and from 1 through 4 carbon atoms in the alkyl moiety alkoxyalkyl wherein the alkoxy and alkyl moieties independently have 1 through 3 carbon atoms or alkylthioalkyl wherein the alkyl moieties independently have 1 through 3 carbon atoms; or $R^1$ and $R^2$ or $R^a$ and $R^b$ together with the nitrogen to which they are joined form a saturated heterocycle having 3- through 6-ring atoms, one of which is the joining nitrogen atom and the remainder of which are carbon atoms, or an unsaturated nitrogen heterocycle selected from the group of 2-pyrrolin-1-yl; 3-pyrrolin-1-yl, 1,2,3,4-tetrahydropyrid-1-yl, and 1,2,5,6-tetrahydropyrid-1-yl;

X is hydrogen, lower alkyl, lower alkoxy, halo, or trifluoromethyl and can be at any available position on the phenyl ring;

Y is lower alkyl, lower alkoxy; halo; lower fluoroalkyl having 1 through 4 carbon atoms and 1 to 3 fluoro atoms; lower fluoroalkoxy having 1 through 4 carbon atoms and 1 through 3 fluoro atoms; or lower fluoroalkylthio having 1 through 4 carbon atoms and 1 through 3 fluoro atoms; with the proviso that when Y is halo then R, $R^1$ and $R^2$ are not all hydrogen and the further proviso that when Y is other than trifluoromethyl and X is other than hydrogen, and $R^1$ is hydrogen and $R^2$ is hydrogen then R is methyl, ethyl, propyl, 2-halophenyl, 2-lower alkylphenyl or 4-fluorophenyl; and Z is

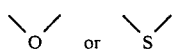

In most instances the starting materials of Formula A will be primary amines, (i.e., $R^a$ and $R^b$ are each hydrogen). However, as the present process effects replacement of the entire amino moiety from compound A with the $R^1R^2N$-radical from the amine reactant the process can be used to replace secondary and tertiary amines of formula A with different secondary or tertiary amines or, by using ammonia, with a primary amine ($H_2N$—). Also, although from the above definitions, it can be seen that $R^1$, $R^2$ and $R^a$, $R^b$ are selected from the same group of substituents, at least one of $R^a$ or $R^b$ must, of course, be different from either $R^1$ or $R^2$ or else both the reactant and product would be the same.

This process can be effected by contacting compound A with a primary or secondary amine (B), having the desired $R^1R^2$ groups or with ammonia, under reactive conditions, preferably in an inert organic solvent and water. More preferably, the process is carried out in the presence of an acid amine salt.

Typically, this process is conducted at temperatures in the range of about from 0° to 250° C., at pressures of about from 1 to 30 atmospheres, for about from 1 to 200 hours using at least about 5 moles of reactant (B) per mole of reactant (A). The selection of optimum reaction conditions within these ranges will generally vary depending on whether a dihydrofuran (Z=O) or dihydrothiophene (Z is S) reactant (A) is used and whether the reaction is conducted in the presence of said acid amine salt.

In the case where reactant A is a dihydrofuran and if an acid amine salt is not used, the process is typically conducted at temperatures in the range of about from 60° to 250° C., preferably about from 65° to 125° C., and more preferably, about 65° to 80° C., at pressures of about from 1 to 30 atmospheres, preferably 1 atmosphere to 15 atmospheres, for about from 1 to 200 hours, preferably about from 1 to 72 hours, using at least 20 moles of amine per mole of compound A. More generally about from 20 to 500, preferably 35 to 300 moles, more preferably, 60 to 300 moles of amine B are used per mole of compound A. Best results are generally obtained using an alcohol solvent. Preferably, the alcohol solvent is a liquid alkanol, for example, methanol, ethanol, and the like. Other inert organic solvents which can be used in place of the alcohol include, for example, tetrahydrofuran, dimethylformamide, dimethylsulfoxide, and the like, and compatible mixtures thereof. Typically, about from 0 to 30, preferably 10 to 20 parts by weight of alcohol or other solvent are used per part by weight of compound A. The process can also be carried out neat (i.e., without solvent).

Best results are typically obtained using aqueous amine. In some instances the amines are supplied commercially as aqueous solutions or the aqueous amine can be formed by adding water directly to the amine and adding the aqueous amine to the reaction mixture or by simply adding water to the reaction mixture. Where an aqueous amine is used, typically about from 0.1 to 10, preferably 0.5 to 4 parts by weight of water are used per part by weight of amine.

It has been found that by conducting this process (Z=O) in the presence of an acid amine salt that generally higher yields are obtained and less rigorous reaction conditions can be used. When the process is conducted in the presence of an acid amine salt, the process can be conducted under the same conditions as given above where the acid amine salt is not used but more typically is conducted at temperatures in the range of about from 0° to 100° C., preferably 20° to 75° C. and pressures in the range of 1 to 30 atmospheres preferably 1 to 10 atmospheres using about from 5 to 50 moles preferably 10 to 20 moles of amine B per mole of compound A (Z=O). (The acid amine salt is generally not used in the case where reactant B is ammonia.) Typically, about from 0.1 to 10 moles, preferably 0.5 to 1 moles, of the acid amine salt are used per mole of compound A. The process is also preferably conducted in the presence of at least a small amount of water. Larger amounts of water (e.g., 0.1 to 50%) generally do not hurt the reaction and the reaction can also be conducted without water. Typically, reaction times on the order of about from 12 to 60 hours are used and more preferably reaction times of about from 12 to 18 can be used. Generally, good results are obtained by simply conducting the process at about atmospheric or ambient pressure.

The term "acid amine salt" refers to acid salts of primary, secondary, and tertiary amines. In terms of the anion, suitable acid amine salts which can be used include, for example, chlorides, bromides, iodides, sulfates, bisulfates, acetates, phosphates and the like. So long as the salt is soluble in the reaction media or water, the particular anion is not critical. On the other hand it is preferred that the organic moiety of the acid amine salt corresponds to the $R^1R^2$ group desired in the product. Since a small amount of the salt will be in equilibrium with amine B the use of salts and amines having different $R^1R^2$ groups can result in the production of a small amount of product II having $R^1R^2$ groups corresponding to the salt. Thus, for example, where amine (B) is methyl amine, preferably the salt should be a methyl ammonium salt ($CH_3NH_3X$). Where the amine B is dimethyl amine, preferably the salt should be a dimethyl or trimethyl ammonium salt (($CH_3)_2NH_2X$ OR ($CH_3)_3NHX$).

The salt can be conveniently prepared in situ by using an excess of amine (B) and adding the appropriate amount of acid to give the desired amount of acid amine salt. (Since a substantial excess of amine is normally used in this process, generally no additional amine is required.) Suitable acids which can be used include, for example, hydrochloric, sulfuric, hydrobromic, hydroiodic, acetic, phosphoric, and the like.

In the case where starting material A is a dihydrothiophene (Z is

)

more rigorous conditions are generally used than where dihydrofurans are used. Thus, in the case of the dihydrothiophenes, the process is typically conducted at temperatures in the range of about from 60° to 250° C., more typically, 100° to 250° C., preferably 100° to 150° C., pressures in the range of about from 1 to 30 atmospheres, more typically 2 to 30 atmospheres, preferably 2 to 20 atmospheres, more preferably 3 to 15 atmospheres, for about from 8 to 100 hours preferably 16 to 36 hours using about from 20 to 500, preferably 35 to 300 moles of amine B per mole of compound A.

The discussion given with respect to the use of an inert organic solvent and water in the dihydrofuran (Z is O) process is also applicable with respect to the dihydrothiophene process (Z is S). Also, as in the case of the dihydrofurans, the dihydrothiophene process can also be advantageously conducted in the presence of an acid amine salt. However, generally the advantages afforded by the use of an acid amine salt in the dihydrothiophene process are not on the same order as afforded in the dihydrofuran process. Thus, typically, even where an acid amine salt is used the dihydrothiophene process will also typically be conducted at temperatures in the range of about from 60° to 250° C., more typically 100° to 250° C., preferably 100° to 150° C., and pressures of about from 1 to 30 atmospheres, preferably 2 to 20 atmospheres, more preferably 3 to 15 atmospheres, for about from 8 to 100 hours, preferably 16 to 36 hours. Typically, about from 0.1 to 10 moles, preferably 0.5 to 1 mole of the acid amine salt and 10 to 50 moles preferably 15 to 30 moles of reactant B are used per mole of reactant A (Z=S).

The more rigorous conditions within the above-described ranges are also typically used in both the furan series and thiophene series when $R^2$ of reactant B is alkoxycarbonyl.

The products of Formula III can be recovered from their respective reaction product mixtures by any suitable separation and purification procedure, such as, for example, recrystallization and chromatography. Suitable separation and purification procedures are, for example, illustrated in the examples set forth hereinbelow.

The starting materials of formula A can be prepared via the procedures described in the aforementioned U.S. application Ser. Nos. 607,610 and 623,805 of C. E. Ward, which descriptions are hereby incorporated by reference.

The amines of Formula B are generally known compounds and can be prepared by known procedures, or obvious modifications thereof (i.e., substitution of appropriate starting materials).

General Process Conditions

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example,

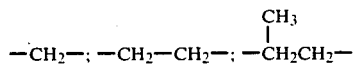

and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight chain or branched chain alkyl groups having 1 through 3 carbon atoms.

The term "lower alkylthioalkyl" refers to the group R'SR"— wherein R' and R" are independently straight chain or branched chain alkyl groups having 1 through 3 carbon atoms.

The term "lower alkoxycarbonylalkyl" refers to the group

wherein R' is lower alkyl and R" is alkylene having 1 through 4 carbon atoms and can be straight or branched chained. Typical alkoxycarbonylalkyl groups include for example, —CH$_2$C(O)OCH$_3$; —CH(CH$_3$)-C(O)OC$_2$H$_5$, and the like.

The term "halo" refers to the group of fluoro, chloro, bromo and iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially then other aryl compounds.

The term "arylalkylene" refers to the group ArR$^3$— wherein Ar is aryl and R$^3$ is alkylene having 1 through 3 carbon atoms and includes both straight-chained and branched-chained alkylenes, for example, methylene, ethyl, 1-methylethyl, and propyl.

The term "(substituted aryl)alkylene" or "ring-substituted arylalkylene" refers to the group Ar'R$^3$— wherein Ar' is substituted aryl and R$^3$ is alkylene as defined with respect to arylalkylene.

The term "saturated nitrogen heterocycle" as used herein with respect to R$^1$ and R$^2$ of formula I refers to the groups having the formula:

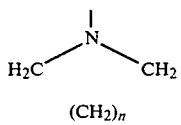

wherein n is 1, 2, or 3.

The term "compatible salts" refers to salts which do not significantly alter the herbicidal properties of the parent compound. Suitable salts include cation salts such as, for example, the cation salts of lithium, sodium, potassium, alkali earth metals.

The term "room temperature" or "ambient temperature" refers to about 20°-25° C.

Utility

As pointed out and more fully described in the aforementioned Ward applications, the compounds of Formula (III) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (III) or mixtures thereof.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the Formula III invention also exhibit plant growth regulating activity and can be used to alter the normal growth pattern of green plants.

A further understanding of the invention can be had in the following non-limiting preparations and examples. Wherein, unless expressly stated to the contrary, all temperatures and temperature ranges refer to the Centigrade system and the term "ambient" or "room temperature" refers to about 20°-25° C. The term "percent" of "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Also where necessary examples are repeated to provide additional starting material for subsequent examples.

EXAMPLES

Preparation A

2-Phenyl-3-oxo-4-(3-trifluoromethylphenyl)-5-amino-2,3-dihydrofuran

This preparation illustrates the preparation of the starting materials of Formula A wherein Z is O, via the procedure described in Ward application Ser. No. 607,610, filed May 9, 1984.

A solution containing 21.8 g of (3-trifluoromethylphenyl)-benzylcarbonyl-acetonitrile, dissolved in 60 ml of acetic acid was treated dropwise with a solution of 12.65 g of bromine in 20 ml of glacial acetic acid. The reaction mixture was stirred for about 16 hours at room temperature. The reaction mixture was poured into 250 ml of water and the resulting mixture was extracted three times with ethyl ether. The organic extracts were washed with saturated aqueous sodium bicarbonate, dried over magnesium sulfate and concentrated in vacuo to yield 8.4 g of white solid which was dried affording 7.0 g of the title compound.

Preparation B

2-Methyl-3-oxo-4-(3-trifluoromethylphenyl)-5-amino-2,3-dihydrothiophene

This preparation illustrates the preparation of the starting materials of Formula A wherein Z is S via the procedure described in C. E. Ward's U.S. application Ser. No. 623,805, filed June 22, 1984.

A solution containing 2.9 g of 1-cyano-1-m-trifluoromethyl-phenyl-(3-methylthio)butan-2-one dissolved in 20 ml of acetic acid was treated with 2 ml of concentrated sulfuric acid. The reaction mixture was refluxed for 30 minutes. The reaction mixture was concentrated in vacuo and chromatographed on silica gel using 2% acetone/dichloromethane as eluent to afford 0.85 g of the title compound.

Example 1

2-Phenyl-3-oxo-4-(3-trifluoromethylphenyl)-5-methylamino-2,3-dihydrofuran

In this example, a mixture containing 0.5 g of 2-phenyl-3-oxo-4-(3-trifluoromethylphenyl)-5-amino-2,3-dihydrofuran ("dihydrofuran starting material") and 25 ml of aqueous 40 wt. % methylamine in 10 ml of methanol was refluxed for 18 hours. The mixture was analyzed by thin-layer chromatography for the dihydrofuran starting material. Another 10 ml of aqueous 40 wt. % methylamine was added and the mixture refluxed for about four hours. The mixture was cooled, poured into 100 ml of water and extracted several times with ethyl ether. The organic extracts were dried over magnesium sulfate, concentrated in vacuo and chromatographed using 3% tetrahydrofuran/chloroform as eluent to yield 0.36 g of the title compound.

Similarly, by applying the same procedure using the corresponding start materials of Formula A, the following compounds can be prepared:

2-phenyl-3-oxo-4-(5-chloro-3-trifluoromethylphenyl)-5-methylamino-2,3-dihydrofuran;
2-phenyl-3-oxo-4-(4-chloro-3-trifluoromethylphenyl)-5-methylamino-2,3-dihydrofuran;
2-phenyl-3-oxo-4-(6-fluoro-3-trifluoromethylphenyl)-5-methylamino-2,3-dihydrofuran;
2-phenyl-3-oxo-4-(4-methyl-3-trifluoromethylphenyl)-5-methylamino-2,3-dihydrofuran;
2-phenyl-3-oxo-4-(5-methoxy-3-trifluoromethylphenyl)-5-methylamino-2,3-dihydrofuran;
2-phenyl-3-oxo-4-(3-difluoromethylphenyl)-5-methylamino-2,3-dihydrofuran;
2-phenyl-3-oxo-4-(3-trifluoromethylthiophenyl)-5-methylamino-2,3-dihydrofuran;
2-(4-fluorophenyl)-3-oxo-4-(3-trifluoromethylphenyl)-5-methylamino-2,3-dihydrofuran;
2-(1-naphthyl)-3-oxo-4-(3-trifluoromethylphenyl)-5-methylamino-2,3-dihydrofuran;
2-phenyl-3-oxo-4-(5-methoxy-3-chlorophenyl)-5-methylamino-2,3-dihydrofuran;
2-phenyl-3-oxo-4-(3,5-diethoxyphenyl)-5-methylamino-2,3-dihydrofuran;
2-(2-nitrophenyl)-3-oxo-4-(3-bromophenyl)-5-methylamino-2,3-dihydrofuran;
2-(1-naphthyl)-3-oxo-4-(3-bromo-2-ethylphenyl)-5-methylamino-2,3-dihydrofuran;
2-phenyl-3-oxo-4-(3-methylphenyl)-5-methylamino-2,3-dihydrofuran;
2-phenyl-3-oxo-4-(3-butoxyphenyl)-5-methylamino-2,3-dihydrofuran;
2-(3-nitrophenyl)-3-oxo-4-(3-iodophenyl)-5-methylamino-2,3-dihydrofuran;
2-(2,3-dichlorobenzyl)-3-oxo-4-(2-trifluoromethylphenyl)-5-methylamino-2,3-dihydrofuran;
2-(3-chloro-8-fluoronaphth-1-yl)-3-oxo-4-(3-trifluoromethylphenyl)-5-methylamino-2,3-dihydrofuran;
2-(2-trifluoromethyl-3-methyl-8-methoxynaphth-1-yl)-3-oxo-4-(3-trifluoromethylphenyl)-5-methylamino-2,3-dihydrofuran;
2-inden-1-yl-3-oxo-4-(3-trifluoromethylphenyl)-5-methylamino-2,3-dihydrofuran;
2-(2-fluoroinden-1-yl)-3-oxo-4-(3-trifluoromethylphenyl)-5-methylamino-2,3-dihydrofuran;
2-methyl-3-oxo-4-(3-trifluoromethylphenyl)-5-methylamino-2,3-dihydrofuran;
2-ethyl-3-oxo-4-(3-trifluoromethylphenyl)-5-methylamino-2,3-dihydrofuran;
2-cyclopentyl-3-oxo-4-(3-trifluoromethylphenyl)-5-methylamino-2,3-dihydrofuran;
2-vinyl-3-oxo-4-(3-trifluoromethylphenyl)-5-methylamino-2,3-dihydrofuran;
2-allyl-3-oxo-4-(3-trifluoromethylphenyl)-5-methylamino-2,3-dihydrofuran;
2-allyl-3-oxo-4-(2-methoxy-3-trifluoromethylphenyl)-5-methylamino-2,3-dihydrofuran;
2-trifluoromethyl-3-oxo-4-(3-trifluoromethylphenyl)-5-methylamino-2,3-dihydrofuran;
2-methyl-3-oxo-4-(3-difluoromethoxyphenyl)-5-methylamino-2,3-dihydrofuran;
2-(2-chlorovinyl)-3-oxo-4-(3-trifluoromethylphenyl)-5-methylamino-2,3-dihydrofuran;
2-methyl-3-oxo-4-(3-trifluoromethylthiophenyl)-5-methylamino-2,3, dihydrofuran;
2-propyl-3-4-(2-methoxy-3-chlorophenyl)-5-methylamino-2,3-dihydrofuran;
2-butyl-3-oxo-4-(2-chloro-3-fluorophenyl)-5-methylamino-2,3-dihydrofuran;
2-benzyl-3-oxo-4-(2-isopropoxy-3-trifluoromethylphenyl)-5-methylamino-2,3-dihydrofuran;
2-naphth-1-yl-3-oxo-4-(3-trifluoromethyl-4-bromophenyl)-5-methylamino-2,3-dihydrofuran;
2-(3-methylphenyl)-3-oxo-4-(3-butyl-4-methylphenyl)-3-oxo-5-methylamino-2,3-dihydrofuran;

2-(3-fluorophenyl)-3-oxo-4-(3-chlorophenyl)-5-methylamino-2,3-dihydrofuran;2-(2,3,5-trifluorophenyl)-3-oxo-4-(3-trifluoromethylphenyl)-5-methylamino-2,3-dihydrofuran; and 2-(3-methylnaphth-1-yl)-3-oxo-4-(3-trifluoromethylphenyl)-5-methylamino-2,3-dihydrofuran;

2-methoxymethylene-3-oxo-4-(3-trifluoromethylphenyl)-5-methylamino-2,3-dihydrofuran;

2-propoxymethylene-3-oxo-4-(3-trifluoromethylphenyl)-5-methylamino-2,3-dihydrofuran;

2-ethoxymethylene-3-oxo-4-(3-trifluoromethylphenyl)-5-methylamino-2,3-dihydrofuran;

2-(2-methoxypropyl)-3-oxo-4-(3-trifluoromethylphenyl)-5-methylamino-2,3-dihydrofuran;

2-methylthiomethylene-3-oxo-4-(3-trifluoromethylphenyl)-5-methylamino-2,3-dihydrofuran;

2-(1-propylthioethyl)-3-oxo-4-(3-trifluoromethylphenyl)-5-methylamino-2,3-dihydrofuran;

2-(2-fluorobenzyl)-3-oxo-4-(3-trifluoromethylphenyl)-5-methylamino-2,3-dihydrofuran;

2-(2-ethoxybenzyl)-3-oxo-4-(3-trifluoromethylphenyl)-5-methylamino-2,3-dihydrofuran;

2-(4-fluorobenzyl)-3-oxo-4-(3-trifluoromethylphenyl)-5-methylamion-2,3-dihydrofuran;

2-(2-trifluoromethylbenzyl)-3-oxo-4-(3-trifluoromethylphenyl)-5-methylamino-2,3-dihydrofuran;

2-(5-chloro-3-propylphenyl)-3-oxo-4-(3-trifluoromethylphenyl)-5-methylamino-2,3-dihydrofuran;

2-(2-nitro-3-methoxyphenyl)-3-oxo-4-(3-trifluoromethylphenyl)-5-methylamino-2,3-dihydrofuran;

2-(2-fluoro-3-2′,2′-dichloroethylenebenzyl)-3-oxo-4-(3-trifluoromethylphenyl)-5-methylamino-2,3-dihydrofuran;

2-(2,3-dichloro-6-methylbenzyl)-3-oxo-4-(3-trifluoromethylphenyl)-5-methylamino-2,3-dihydrofuran;

2-(beta-phenethyl)-3-oxo-4-(3-trifluoromethylphenyl)-5-methylamino-2,3-dihydrofuran;

2-[3-(2-bromophenyl)propyl]-3-oxo-4-(3-trifluoromethylphenyl)-5-methylamino-2,3-dihydrofuran;

2-[1-methyl-2-(phenyl)ethyl]-3-oxo-4-(3-trifluoromethylphenyl)-5-methylamino-2,3-dihydrofuran;

2-naphth-1-ylmethylene-3-oxo-4-(3-trifluoromethylphenyl)-5-methylamino-2,3-dihydrofuran;

2-(2-fluoronaphth-1-ylmethylene)-3-oxo-4-(3-trifluoromethylphenyl)-5-methylamino-2,3-dihydrofuran;

2-(2-chloro-8-methylnaphth-1-ylmethylene)-3-oxo-4-(3-trifluoromethylphenyl)-5-methylamino-2,3-dihydrofuran;

2-(3-methoxy-5-nitro-7-fluoromethylnaphth-1-yl)-3-oxo-4-(3-trifluoromethylphenyl)-5-methylamino-2,3-dihydrofuran;

2-(beta-naphth-1-ylethyl)-3-oxo-4-(3-trifluoromethylphenyl)-5-methylamino-2,3-dihydrofuran;

2-[beta-(8-fluoronaphth-1-yl)ethyl]-3-oxo-4-(3-trifluoromethylphenyl)-5-methylamino-2,3-dihydrofuran;

2-[1-(7-methoxynaphth-1-yl)ethyl]-3-oxo-4-(3-trifluoromethylphenyl)-5-methylamino-2,3-dihydrofuran;

2-inden-1-ylmethylene-3-oxo-4-(3-trifluoromethylphenyl)-5-methylamino-2,3-dihydrofuran; and 2-(2-fluoroinden-1-ylmethylene)-3-oxo-4-(3-trifluoromethylphenyl)-5-methylamino-2,3-dihydrofuran.

Similarly, by applying the same procedure but respectively using aqueous solutions of ethylamine, butylamine; allylamine; methoxycarbonylmethylene amine; methoxymethylene amine; ethylthioethylamine; dimethyl amine; N-methyl-N-allylamine; N-methyl-N-methoxycarbonylmethylene amine; N-methyl-N-methoxymethylene amine; N-methyl-N-ethylthioethyl amine; 2-pyrroline; 1,2,3,4-tetrahydropyridine, pyrrolidine, and piperidine, the corresponding 2-substituted amino analogs of each of the above compounds can be prepared, for example, (also where methoxycarbonylmethylene amine and N-methyl-N-methoxycarbonylmethylene are used both the reaction temperature and pressure are preferably increased):

2-phenyl-3-oxo-4-(3-trifluoromethylphenyl)-5-ethylamino-2,3-dihydrofuran;

2-methyl-3-oxo-4-(3-trifluoromethylphenyl)-5-butylamino-2,3-dihydrofuran;

2-ethyl-3-oxo-4-(3-trifluoromethylphenyl)-5-allylamino-2,3-dihydrofuran;

2-phenyl-3-oxo-4-(3-trifluoromethylphenyl)-5-methoxycarbonylmethylamino-2,3-dihydrofuran;

2-methyl-3-oxo-4-(3-trifluoromethylphenyl)-5-methoxymethylamino-2,3-dihydrofuran;

2-methyl-3-oxo-4-(3-trifluoromethylphenyl)-5-ethylthioethylamino-2,3-dihydrofuran;

2-ethoxymethylene-3-oxo-4-(3-trifluoromethylphenyl)-5-dimethylamino-2,3-dihydrofuran;

2-ethyl-3-oxo-4-(3-trifluoromethylphenyl)-5-(N-methyl-N-allylamino)-2,3-dihydrofuran;

2-phenyl-3-oxo-4-(3-trifluoromethylphenyl)-5-(N-methyl-N-methoxycarbonylmethylamino)-2,3-dihydrofuran;

2-methyl-3-oxo-4-(3-trifluoromethylphenyl)-5-(N-methyl-N-methoxymethylamino)-2,3-dihydrofuran;

2-methylthiomethylene-3-oxo-4-(3-trifluoromethylphenyl)-5-(N-methyl-N-ethylthioethylamino-2,3-dihydrofuran;

2-ethyl-3-oxo-4-(3-trifluoromethylphenyl)-5-(2-pyrrolin-1-yl)-2,3-dihydrofuran;

2-phenyl-3-oxo-4-(3-trifluoromethylphenyl)-5-(1,2,3,4-tetrahydropyrid-1-yl)-2,3-dihydrofuran;

2-methyl-3-oxo-4-(3-trifluoromethylphenyl)-5-pyrrolidin-1-yl-2,3-dihydrofuran;

2-ethyl-3-oxo-4-(3-trifluoromethylphenyl)-5-piperidin-1-yl-2,3-dihydrofuran; etc.

Example 2

2-Phenyl-3-Oxo-4-(3-Trifluoromethylphenyl)-5-Methylamino-2,3-Dihydrofuran

In this example, 2 g of methylammonium chloride was added at room temperature to a stirred slurry containing 10 g of 2-phenyl-3-oxo-4-(3-trifluoromethylphenyl)-5-amino-2,3-dihydrofuran in 60 ml of aqueous 40 wt % methyl amine followed by the addition of 50 ml of methanol. The resulting suspension was heated to reflux and refluxed overnight (about 15—18 hours). The mixture was cooled to room temperature and added to a dilute acid solution containing 58 ml of aqueous 12N hydrochloric acid in 300 ml of water. This mixture was extracted twice with methylene chloride. The methylene chloride extracts were combined and successively washed once with water, once with saturated aqueous sodium bicarbonate and once with saturated aqueous sodium chloride. The washed solution was dried over magnesium sulfate and evaporated under vacuum affording 9.2 g of the title compound as a pale yellow foam (yield=88%).

Similarly, by using the appropriate starting materials, this process can be applied to prepare the products listed in Example 1.

Example 3

2-Phenyl-3-Oxo-4-(3-Trifluoromethylphenyl)-5-Methylamino-2,3-Dihydrofuran

This example illustrates a procedure similar to Example 2, hereinabove, but in which the acid amine salt is prepared in situ.

In this example, 2.5 ml of aqueous 2N hydrochloric acid was added at room temperature to a stirred slurry containing 10 g of 2-phenyl-3-oxo-4-(3-trifluoromethylphenyl)-5-amino-2,3-dihydrofuran in 60 ml of aqueous 40 wt % methyl amine followed by the addition of 50 ml of methanol. The resulting suspension was heated to reflux and refluxed for about 24 hours and then allowed to cool and stand at room temperature for about 2 days. The mixture was then added to a dilute acid solution containing 58 ml of aqueous 12N hydrochloric acid in 300 ml of water and then extracted twice with methylene chloride. The methylene chloride extracts were combined and successively washed once with water, once with saturated aqueous sodium bicarbonate and once with saturated aqueous sodium chloride. The washed solution was dried over magnesium sulfate and evaporated under vacuum affording 9.7 g of the title compound as a pale yellow foam (yield=93%).

Similarly, by using the appropriate starting materials, this process can be applied to prepare the product listed in Example 1.

Example 3

2-Methyl-3-oxo-4-(3-trifluoromethylphenyl)-5-methylamino-2,3-dihydrothiophene In this example a mixture containing 5.46 g of 2-methyl-3-oxo-4-(3-trifluoromethylphenyl)-5-amino-2,3-dihydrothiophene; 6.2 g of methyl amine; 9.30 g of water in 20 ml of methanol was placed in a sealed pressure vessel (steel bomb) and heated for 18 hours at 105° C.; then 18 hours at 120° C.; and then 18 hours at 115° C. The mixture was diluted with water and extracted three times with dichloroethane. The extracts were combined and then washed with water, dried over magnesium sulfate and then evaporated affording the title compound as an impure oil residue which was then purified by chromatography over silica gel eluting with methanol:-chloroform.

Similarly, by applying the same procedure but using the corresponding 2,3-dihydrothiophene starting material, the corresponding 2,3-dihydrothiophene analogs of the 2,3-dihydrofuran products enumerated in Example 1 can be prepared.

Similarly, by applying the same procedure but respectively using aqueous solutions of ethylamine; butylamine; allylamine; methoxycarbonylmethylene amine; methoxymethylene amine; ethylthioethylamine; dimethyl amine; N-methyl-N-allylamine; N-methyl-N-methoxycarbonylmethylene amine; N-methyl-N-methoxymethylene amine; N-methyl-N-ethylthioethyl amine; 2-pyrroline; 1,2,3,4-tetrahydropyridine, pyrrolidine, and piperidine, the corresponding 2-substututed amine analogs of each of the above compounds can be prepared, for example, (also where methoxycarbonylmethylene amine and N-methyl-N-methoxycarbonylmethylene are used both the reaction temperature and pressure are preferably increased still further):

2-phenyl-3-oxo-4-(3-trifluoromethylphenyl)-5-ethylamino-2,3-dihydrothiophene;
2-methyl-3-oxo-4-(3-trifluoromethylphenyl)-5-butylamino-2,3-dihydrothiophene;
2-ethyl-3-oxo-4-(3-trifluoromethylphenyl)-5-allylamino-2,3-dihydrothiophene;
2-phenyl-3-oxo-4-(3-trifluoromethylphenyl)-5-methoxycarbonylmethylamino-2,3-dihydrothiophene;
2-methyl-3-oxo-4-(3-trifluoromethylphenyl)-5-methoxymethylamino-2,3-dihydrothiophene;
2-methyl-3-oxo-4-(3-trifluoromethylphenyl)-5-ethylthioethylamino-2,3-dihydrothiophene;
2-ethoxymethylene-3-oxo-4-(3-trifluoromethylphenyl)-5-dimethylamino-2,3-dihydrothiophene;
2-ethyl-3-oxo-4-(3-trifluoromethylphenyl)-5-(N-methyl-N-allylamino)-2,3-dihydrothiophene;
2-phenyl-3-oxo-4-(3-trifluoromethylphenyl)-5-(N-methyl-N-methoxycarbonylmethylamino)-2,3-dihydrothiophene;
2-methyl-3-oxo-4-(3-trifluoromethylphenyl)-5-(N-methyl-N-methoxymethylamino)-2,3-dihydrothiophene;
2-methylthiomethylene-3-oxo-4-(3-trifluoromethylphenyl)-5-(N-methyl-N-ethylthioethylamino-2,3-dihydrothiophene;
2-ethyl-3-oxo-4-(3-trifluoromethylphenyl)-5-(2-pyrrolin-1-yl)-2,3-dihydrothiophene;
2-phenyl-3-oxo-4-(3-trifluoromethylphenyl)-5-(1,2,3,4-tetrahydropyrid-1-yl)-2,3-dihydrothiophene;
2-methyl-3-oxo-4-(3-trifluoromethylphenyl)-5-pyrrolidin-1-yl-2,3-dihydrothiophene;
2-ethyl-3-oxo-4-(3-trifluoromethylphenyl)-5-piperidin-1-yl-2,3-dihydrothiophene; etc.

Obviously, many modifications and variations of the invention described hereinabove and below can be made without departing from the essence and scope thereof.

What is claimed is:

1. A process for preparing a compound having the formula:

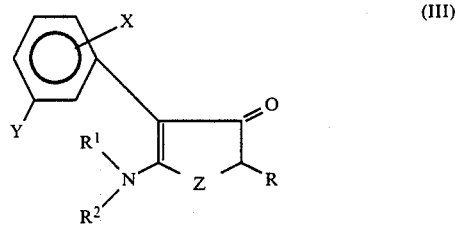

(III)

wherein R is lower alkyl, having 1 through 4 carbon atoms; cycloalkyl having 3 through 7 carbon atoms, lower alkenyl; fluoroalkyl having 1 through 4 carbon atoms and 1 through 3 fluoro atoms; haloalkenyl having 2 through 4 carbon atoms and 1 through 3 halo atoms independently selected from the group of fluoro, chloro, bromo, or iodo and wherein the halo atom is on a double bond carbon atom; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

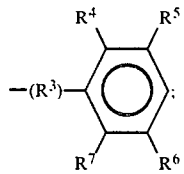

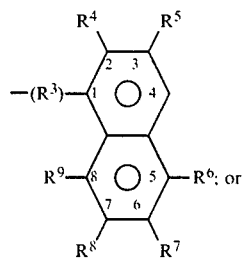

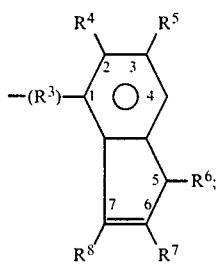

wherein
one, two or three of $R^4$, $R^5$, $R^6$, $R^7$, $R^8$, and $R^9$ are independently selected from the group of lower alkyl, lower alkoxy, halo, nitro, or fluoroalkyl having 1 through 3 carbon atoms and 1 through 3 fluoro atoms, and the remainder are hydrogen; and $R^3$ is a single bond or alkylene having 1 through 3 carbon atoms;
$R^1$ is hydrogen or alkyl having 1 through 4 carbon atoms;
$R^2$ is hydrogen, alkyl having 1 through 4 carbon atoms, alkenylmethylene having 3 or 4 carbon atoms, lower alkoxycarbonylalkyl, lower alkoxyalkyl or lower alkylthioalkyl; or
$R^1$ and $R^2$ together with the nitrogen atom to which they are joined form a saturated heterocycle having 3 through 6-ring atoms one of which is the joining ring nitrogen atom and the remainder of which are carbon atoms or an unsaturated nitrogen heterocycle selected from the group of 2-pyrrolin-1-yl; 3-pyrrolin-1-yl; 1,2,3,4-tetrahydropyrid-1-yl and 1,2,5,6-tetrahydropyrid-1-yl;
X is hydrogen, lower alkyl, lower alkoxy, halo, or trifluoromethyl and can be at any available position on the phenyl ring;
Y is lower alkyl, lower alkoxy, halo, lower fluoroalkyl having 1 through 4 carbon atoms and 1 through 3 fluoro atoms, lower haloalkoxy having 1 through 4 carbon atoms and 1 through 3 fluoro atoms, or lower fluoroalkylthio having 1 through 4 carbon atoms and 1 through 3 fluoro atoms, with the proviso that when Y is halo then R, $R^1$ and $R^2$ are not all hydrogen and the further proviso that when Y is other than trifluoromethyl and X is other than hydrogen, and $R^1$ and $R^2$ are each hydrogen then R is methyl, ethyl, propyl, 2-halophenyl, 2-lower alkylphenyl or 4-fluorophenyl; and Z is O or S, which comprises contacting a compound having the formula:

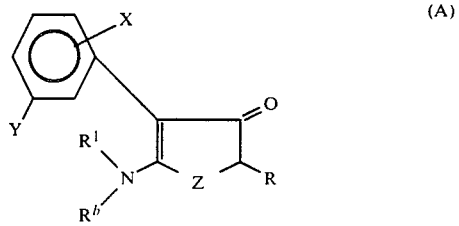

wherein
R, Z, X, and Y are as defined hereinabove and $R^a$ and $R^b$ are selected from the same group of substituents as defined for $R^1$ and $R^2$ with the proviso that $R^a$ is a different group than either $R^1$ or $R^2$;
with a compound having the formula $R^1R^2NH$ (B)
wherein
$R^1$ and $R^2$ are as defined hereinabove,
under reactive conditions at temperatures in the range of about from 0° to 250° C. and pressures of about from 1 atmosphere to 30 atmospheres using at least about 5 moles of the compound of Formula B per mole of compound of formula A.

2. The process of claim 1 wherein an aqueous solution of said amine is used.

3. The process of claim 1 wherein said process is conducted in an inert organic solvent.

4. The process of claim 3 wherein said solvent is a liquid alkanol.

5. The process of claim 4 wherein said alkanol is methanol or ethanol.

6. The process of claim 1 wherein $R^a$ and $R^b$ are each hydrogen.

7. The process of claim 2 wherein $R^a$ and $R^b$ are each hydrogen.

8. The process of claim 5 wherein Z is oxa and said process is conducted at temperatures in the range of about from 65° to 125° C. using about from 20 to 500 moles of Compound B per mole of Compound A.

9. The process of claim 8 wherein an aqueous solution of said amine is used.

10. The process of claim 9 wherein said process is conducted in an inert organic solvent.

11. The process of claim 9 wherein said solvent is a liquid alkanol.

12. The process of claim 1 wherein Z is oxa and $R^1$ or $R^2$ are not both hydrogen and therein said process is conducted in an inert solvent and in the presence of an acid salt of a primary, secondary, or tertiary amine.

13. The process of claim 12 wherein said process is conducted at temperatures in the range of about from 0° to 100°.

14. The process of claim 13 wherein said process is conducted in the presence of about from 0.1 to 10 moles of said acid salt of an amine per mole of Compound A, using about 5 to 50 moles of Compound B per mole of Compound A.

15. The process of claim 13 wherein the organic moiety of said acid salt of an amine corresponds to the $R^1R^2$ substituent of Compound B.

16. The process of claim 14 wherein said process is conducted at about atmospheric pressure and temperatures in the range of about from 20° to 25° C.

17. The process of claim 14 wherein said process is conducted in the presence of about from 0.1 to 1 mole of said acid amine salt per mole of Compound A.

18. The process of claim 17 wherein said process is conducted at temperatures in the range of about from 20° to 75° C. and wherein Compound B is methylamine or ethylamine and wherein when said Compound B is methylamine said acid salt of an amine is a methylammonium salt and wherein said Compound B is ethylamine, said acid salt of an amine is an ethylammonium salt.

19. The process of claim 18 wherein said Compound B is methylamine and said methylammonium salt is methylammonium chloride.

20. The process of claim 1 wherein Z is thia and said process is conducted at temperatures in the range of about from 100° to 250° C. and pressures in the range of about from 2 to 20 atmospheres.

21. The process of claim 20 wherein about from 20 to 500 moles of Compound B are used per mole of Compound A.

22. The process of claim 21 wherein an aqueous solution of said amine is used.

23. The process of claim 21 wherein said process is conducted in an inert organic solvent.

24. The process of claim 23 wherein said inert organic solvent is a liquid alkanol.

25. The process of claim 20 wherein about from 35 to 300 moles of said amine are used per mole of compound A.

26. The process of claim 25 wherein said process is conducted at temperatures in the range of 100° to 150° C. and pressures in the range of about from 3 to 15 atmospheres.

27. The process of claim 20 wherein said process is conducted in the presence of about from 0.1 to 10 moles of an acid salt of a primary, secondary, or tertiary amine per mole of Compound A and wherein said process is conducted in an inert organic solvent.

28. The process of claim 27 wherein said process is conducted using 10 to 50 moles of Compound B per mole of Compound A.

29. The process of claim 28 wherein an aqueous solution of said Compound B is used.

30. The process of claim 29 wherein said process is conducted at temperatures in the range of about from 100° to 150° C. using about from 0.5 to 1 mole of said acid salt of an amine per mole of Compound A.

31. The process of claim 1 wherein $R^2$ is alkyl having 1 to 4 carbon atoms, alkenylmethylene having 3 or 4 carbon atoms; lower alkoxyalkyl, lower alkylthioalkyl or $R^1$ and $R^2$ together with the nitrogen atom to which they are joined, form said saturated or unsaturated heterocycle.

32. The process of claim 5, wherein $R^2$ is alkyl, or alkenylmethylene.

33. The process of claim 5 wherein $R^1$ is hydrogen and $R^2$ is alkyl.

* * * * *